United States Patent [19]

Cheong

[11] Patent Number: 5,441,741
[45] Date of Patent: Aug. 15, 1995

[54] FREEZE-DRIED PAD

[75] Inventor: Catherine L. Cheong, Burnley, United Kingdom

[73] Assignee: Johnson & Johnson Medical, Inc., Arlington, Tex.

[21] Appl. No.: 35,014

[22] Filed: Mar. 22, 1993

[30] Foreign Application Priority Data

Apr. 30, 1992 [GB] United Kingdom ............ 9209327

[51] Int. Cl.$^6$ .............................................. A61L 15/00
[52] U.S. Cl. ................................ 424/402; 424/78.06; 424/443; 424/445; 424/446; 424/447
[58] Field of Search ............ 424/400, 443, 445, 446, 424/447, 402, 78.06

[56] References Cited

U.S. PATENT DOCUMENTS

| | | | |
|---|---|---|---|
| 4,292,972 | 10/1981 | Pawelchak et al. | 128/296 |
| 4,965,203 | 10/1990 | Silbering et al. | 424/446 |
| 5,206,026 | 4/1993 | Sharik | 424/447 |
| 5,206,028 | 4/1993 | Li | 424/447 |

FOREIGN PATENT DOCUMENTS

WO91/19480 12/1991 European Pat. Off. ....... A61K 9/06
55-083710 12/1978 Japan .

OTHER PUBLICATIONS

Abstract for enzyme-containing spongy material comprising polymer which is water soluble or converts to viscous gel on contact with water.

Primary Examiner—Thurman K. Page
Assistant Examiner—Amy Hulina
Attorney, Agent, or Firm—James Riesenfeld

[57] ABSTRACT

There is disclosed: an absorbent, non-adherent, freeze-dried, fibre-free pad comprising from 2 to 6 parts by weight of a water-soluble biocompatible polymer and from 2 to 15 parts by weight of a liquid humectant, provided that the weight ratio of humectant to polymer is from 0.75:1 to 2.5:1 and; a method for producing the pad.

21 Claims, No Drawings

FREEZE-DRIED PAD

The present invention relates to a pad particularly, but not exclusively, for medical use. The pad may be used as an absorbent or a wound-contacting layer on both wet and dry wounds.

In treating wounds, such as cuts, grazes, abrasions, ulcers and burns, it is generally necessary to cover the wound in order to promote wound healing and to prevent the wound from becoming infected. It is often necessary to absorb material exuding from the wound to keep the wound as dry as possible.

There are available a wide variety of dressings which can be applied to wounds, ranging from common sticking plasters through to large size sheets for application to extensive burns. These dressings vary in the types of materials used and the arrangement of the materials in the dressing. However, they all have in common the fact that one layer of the dressing will come into contact with the wound.

It is desirable that the wound-contacting layer in the dressing should be non-adherent and should be conformable so that it can be easily applied and removed. However, many of the wound-contacting layers at present known are not very conformable and in some cases are adherent. Particularly where the wound contacting layer contains a fibrous component, it is often the case that the wound-contacting layer will become stuck to the wound by dried exudate or by the formation of a scab around the fibres in the wound-contacting layer. This is a significant disadvantage as it prevents the dressing from being removed without damaging the wound and causing discomfort to the patient.

Another form of dressing uses a non-fibrous sheet comprising a water insoluble hydrogel (superabsorbent) as the main structural material. Such hydrogel sheets are generally dry as produced and can be applied directly to a wound. They are then able to absorb exudate from the wound. However, if they are left too long on a wound, they tend to dry out, leaving a dry pellicle attached to the wound. This dry pellicle is difficult to remove from the wound without causing damage and without causing discomfort to the patient. Even if the hydrogel sheet does not dry out to form a pellicle, it can still be very difficult to remove from a wound as it can become stuck on the wound.

It is useful for a wound-contacting layer to be absorbent, although in many dressings this is not the case. The material from which such absorbent wound-contacting layers are made can also be of use in other contexts, for instance as swabs for cleaning up wounds and the surrounding areas before a dressing is applied or for mopping up liquids both in medical and non-medical applications.

WO-A-91/19480 discloses a system for the topical delivery of medicaments. The delivery system comprises a compressed, freeze-dried pad containing a medicament such as a growth hormone. The freeze-dried pad comprises a base material such as certain specific water-soluble cellulose ether compounds. The pad may in addition include a solid polyethylene glycol having a molecular weight of at least 3,000 as a bulking agent.

The present invention relates to the discovery of a material which can be used as a wound-contacting layer and as an absorbent pad for a number of other uses.

According to the present invention, there is provided an absorbent, non-adherent, freeze-dried, fibre-free pad comprising from 2 to 6 parts by weight of a water-soluble biocompatible polymer and from 2 to 15 parts by weight of a liquid humectant, provided that the weight ratio of humectant to polymer is from 0.75:1 to 2.5:1.

If the humectant to polymer weight ratio is below 0.75:1, then the pad will be too inflexible for use as a wound contacting layer. If the ratio substantially exceeds 2.5:1, the product does not remain dry to the touch following irradiation since the humectant will then have a tendency to leach out. Preferably, the humectant to polymer weight ratio is from about 1:1 to about 2:1.

Suitable water-soluble polymers include hydroxyethyl cellulose, carboxymethyl cellulose, polyvinyl pyrrolidone and sodium and potassium alginates. These may be used alone or in mixtures. The preferred polymer is hydroxyethyl cellulose.

Suitable liquid humectants are low molecular weight hydrophilic materials. (These humectants must be liquids at room temperature (about 25° C.)). Preferred liquid humectants include glycerol, propylene glycol and low molecular weight polyethylene glycols generally having molecular weights below 600. These may be used alone or in mixtures. A particularly preferred humectant is a mixture of glycerol and propylene glycol.

The pad of the present invention may further include a medicament such as: chlorhexidine or one of its derivatives, for example chlorhexidine hydrochloride, acetate or gluconate; povidone-iodine; a quaternary ammonium salt such as cetyl pyridinium chloride; silver sulphur diazine; a local anaesthetic; a growth factor; a glycosaminoglycan; or a matrix protein. Suitable glycosaminoglycans include hyaluronic acid, chondroitin 4 sulphate, chondroitin 6 sulphate, keratan sulphate and heparan sulphate. Suitable matrix proteins include fibronectin, laminin and collagen.

It is particularly advantageous to include soluble collagen in the pad of the present invention. The soluble collagen provides wound compatibility and promotes wound healing by providing a readily available supply of collagen protein for use in a number of biochemical wound healing pathways. Collagen is also absorbent and can therefore contribute to the absorbency of the pad. The soluble collagen preferably comprises up to 10% of the pad and most preferably comprises from 1 to 5% of the pad.

Preferably, when soluble collagen is included in the pad, the polymer used is an alginate.

Alternatively, it is advantageous to include hyaluronic acid in the pad. Hyaluronic acid acts to promote healing and in effect acts as a growth factor. Preferably the hyaluronic acid comprises up to 1% of the pad and most preferably, comprises from 0.1 to 0.5% of the pad.

The pad may also contain an enzyme or enzymes. Particularly useful enzymes are proteases which can be used to assist in debriding (the removal of dead tissue).

The pads of the present invention may, if desired, include preservatives, such as hydroxybenzoates, including methyl p-hydroxybenzoate and propyl p-hydroxybenzoate, in order to improve their shelf life.

Preferably, the pads of the present invention are packaged in sealed pouches and sterilized, advantageously by use of gamma irradiation.

The pads of the present invention have a number of advantageous properties. After freeze drying, and irradiation if used, the pads remain dry to touch, thus showing that humectant does not leak out of the pad. The pad is thus stable. Since the polymer and the humectant are hydrophilic, the pads are absorbent. Even though the pad has been freeze-dried, it is highly conformable and can thus be applied easily to a variety of wound sites. The pad remains pliable even if it is left in place for a long time. It does not form a dry pellicle.

The pad of the present invention is of particular use as a wound-contacting layer because it can be readily removed from a wound, i.e. it is non-adherent, however far the healing process has proceeded. All that is required is the gentle application of water or a saline solution, which will dissolve the pad and thus remove it from the wound. In some instances, it will not be necessary to remove the pad as it will dissolve in the exudate from the wound. In such cases it will only be necessary to replace the pad until the wound dries out.

The pads of the present invention may also include particulate water-insoluble materials provided these can be washed away once the remainder of the pad has been dissolved. Suitable particulate materials include calcium alginate, which is useful as a haemostat. This material is of particular use in a pad wherein the water-soluble polymer is sodium or potassium alginate. Calcium alginate can readily be washed away with a saline solution which converts insoluble calcium alginate to soluble sodium alginate.

The pad of the present invention is strong and robust when dry, despite the fact that it has been freeze-dried. It is not friable and therefore does not shed particles into the wound. It does not contain any fibres and therefore cannot provide any fibres which, if present, could interfere with wound healing.

The pad of the present invention will be of particular use in removing dead skin from around a wound, especially, but not only, where it contains a debriding enzyme. For instance, the pad may be moistened and then applied to the dead skin. The moisture, together with the enzyme if present, will cause the removal of dead tissue.

According to a second aspect of the invention, there is provided a method for producing an absorbent pad which comprises freeze drying an aqueous solution comprising from 2 to 6 parts by weight of a water soluble biocompatible polymer and from 2 to 15 parts by weight of a humectant, provided that the weight ratio of humectant to polymer is from 0.75 to 2.5:1.

Preferably, the solution contains sufficient water to make the total weight up to about 100 parts.

The aqueous solution may contain any of the materials or additional materials referred to above with reference to the pad of the present invention.

The aqueous solution is produced by mixing the water-soluble polymer, humectants and water together until a homogeneous solution (or dispersion if an insoluble particulate material is added) is produced. The order of mixing will depend on the particular components used in each case.

Advantageously, a thin layer of the aqueous solution is produced and freeze-dried so as to produce the pad in sheet form. Such a sheet is generally white, fluffy, soft and conformable with a suede-like feel. Alternatively, a thick layer may be freeze-dried to produce a protective absorbent pad.

Preferably, the method includes the steps of sealing the pad in a pouch and sterilizing the pad, advantageously by gamma irradiation. On irradiation, the pad becomes slightly less fluffy and somewhat more compact.

The aqueous solution may be freeze-dried using any suitable apparatus. Such apparatus requires means to freeze the solution and means for applying substantially reduced pressure to the frozen solution. Such apparatus is commercially available and does not form part of the present invention.

The present invention is illustrated by the following examples, which are not intended to place any limitation on the scope of the invention.

EXAMPLE 1

3 parts by weight of glycerol and 1 part of propylene glycol were mixed together. To this mixture was added 4 parts of hydroxyethyl cellulose (Natrosol 250 HX Pharm., supplied by Aqualon (UK) Limited, having a viscosity as a 1% solution at 25° C. of 1500 to 2500 mPa.s). The components were mixed together using a spatula. 92 parts of water were added to the mixture and mixing with the spatula was continued until a homogeneous solution was formed.

The solution was poured into a stainless steel tray to a depth of 1 mm. The solution was then frozen using a Virtis Freeze Mobile SL12 apparatus. The apparatus then applied a pressure of 0.05 mbar over the frozen solution for a period of 24 hours. At the end of this time, substantially all the water had been removed from the solution, leaving a white, fluffy, very soft and conformable sheet-like pad.

The pad was sealed in a pouch and subject to a dose of 25 Mrad of gamma irradiation. The pad after irradiation was less fluffy and more compact than the unirradiated pad.

The final pad was dry to the touch, absorbent, conformable, strong, robust and non-friable. It could be applied to wounds readily and could be removed easily merely by applying water or a saline solution. The pad could be left exposed for a considerable time without drying out or losing any humectant.

EXAMPLE 2

4 parts by weight of polyethylene glycol 400, which is a liquid at room temperature, and 92 parts of water were mixed together. To this mixture was added 4 parts of hydroxyethyl cellulose (Natrosol 250 HX Pharm.). The components were mixed together using a spatula until a homogeneous solution was formed.

The solution was poured into a stainless steel tray to a depth of 10 mm. The solution was then freeze-dried and irradiated as described in Example 1.

The final pad was a soft, highly absorbent, strong, compressible sponge-like material, suitable for applying to highly exuding wounds giving protection, absorbency and non-adherence.

EXAMPLE 3

4 parts of glycerol and 2 part of propylene glycol were mixed together. To this mixture was added 4 parts of sodium alginate (Protanal LF 10/60 having a viscosity at 25° C. of 40 to 70 mPa.s as a 1% aqueous solution and conforming to all the quality requirements of the European Pharmacopoeia). To this mixture was added 0.25 parts of soluble collagen (Bovine type I collagen supplied by LabImpex). Finally 89.75 parts of water were added. The components were mixed together, poured to a depth of 10 mm, freeze-dried and irradiated as described in Example 2. The final pad was as described in Example 2 and contained approximately 2.4% soluble collagen.

EXAMPLE 4

Example 3 was repeated except that 0.02 parts of water were replaced by 0.02 parts of hyaluronic acid. The pad thus produced has the properties described in Example 2 and contained approximately 0.19% hyaluronic acid.

EXAMPLE 5

Example 2 was repeated except that 0.02 parts of the water were replaced by 0.02 parts of a debriding enzyme. The pad had the properties set out in Example 2 and contained approximately 0.25% of a debriding enzyme.

It will be appreciated that the present invention has been described above by way of example only and that modifications and alterations can be made by the skilled man without departing from the scope of the invention.

We claim:

1. An absorbent, non-adherent, freeze-dried, fibre-free pad comprising from 2 to 6 parts by weight of a water-soluble biocompatible polymer, selected from the group consisting of soluble cellulosics, polyvinyl pyrrolidone, soluble alginates, and mixtures thereof, and from 2 to 15 parts by weight of a liquid humectant, said liquid humectant being a liquid at room temperature, provided that the weight ratio of humectant to polymer is from 0.75:1 to 2.5:1.

2. The pad of claim 1, wherein the weight ratio is from 1:1 to 2:1.

3. The pad of claim 1, wherein the water-soluble polymer is selected from the group consisting of hydroxyethyl cellulose, carboxymethyl cellulose, polyvinyl pyrrolidone, sodium and potassium alginates and mixtures thereof.

4. The pad of claim 3, wherein the polymer is hydroxyethyl cellulose.

5. The pad of claim 1, wherein the humectant is selected from the group consisting of glycerol, propylene glycol, low molecular weight polyethylene glycols and mixtures thereof.

6. The pad of claim 5, wherein the humectant is a mixture of glycerol and propylene glycol.

7. The pad of claim 1, further including a medicament selected from the group consisting of chlorhexidine and its derivatives; povidone-iodine; quaternary ammonium salts; silver sulphur diazine; local anaesthetics; growth factors; glycosaminoglycans; matrix proteins; and enzymes.

8. The pad of claim 1, further including a preservative.

9. The pad of claim 1, further including a particulate water-insoluble material.

10. The pad of claim 1, which is packaged in a sealed pouch and sterilized.

11. A method for producing an absorbent pad which comprises freeze drying an aqueous solution comprising from 2 to 6 parts by weight of a water soluble biocompatible polymer, selected from the group consisting of soluble cellulosics, polyvinyl pyrrolidone, soluble alginates, and mixtures thereof, and from 2 to 15 parts by weight of a liquid humectant, said liquid humectant being a liquid at room temperature, provided that the weight ratio of humectant to polymer is from 0.75:1 to 2.5:1.

12. The method of claim 11, wherein the solution contains sufficient water to make the total weight up to about 100 parts.

13. The method of claim 11, wherein the weight ratio is from 1:1 to 2:1.

14. The method of claim 11, wherein the water-soluble polymer is selected from the group consisting of hydroxyethyl cellulose, carboxymethyl cellulose, polyvinyl pyrrolidone, sodium and potassium alginates and mixtures thereof.

15. The method of claim 14, wherein the polymer is hydroxyethyl cellulose.

16. The method of claim 11, wherein the humectant is selected from the group consisting of glycerol, propylene glycol, low molecular weight polyethylene glycols and mixtures thereof.

17. The method of claim 11, wherein the humectant is a mixture of glycerol and propylene glycol.

18. The method of claim 11, wherein the solution further includes a medicament selected from the group consisting of chlorhexidine and its derivatives; povidone-iodine; quaternary ammonium salts; silver sulphur diazine; local anaesthetics; growth factors; glycosaminoglycans; matrix proteins; and enzymes.

19. The method of claim 11, wherein the solution further includes a preservative.

20. The method of claim 11, wherein the solution further includes a particulate water-insoluble material.

21. The method of claim 11, which includes the steps of packaging the pad in a sealed pouch and sterilizing the pad.

* * * * *